United States Patent [19]
Taheri

[11] Patent Number: 5,968,057
[45] Date of Patent: Oct. 19, 1999

[54] APPARATUS FOR REMOVING A BLOOD CLOT FROM A VESSEL

[76] Inventor: Syde A. Taheri, 268 Dan Troy, Williamsville, N.Y. 14221

[21] Appl. No.: 08/878,049

[22] Filed: Jun. 18, 1997

[51] Int. Cl.$^6$ .................................................. A61B 17/22
[52] U.S. Cl. ............................ 606/159; 606/127; 606/200
[58] Field of Search ................................... 606/159, 127, 606/200

[56] References Cited

U.S. PATENT DOCUMENTS

| | | | |
|---|---|---|---|
| 4,509,517 | 4/1985 | Zibelin | 606/127 |
| 4,706,671 | 11/1987 | Weinrib | 606/159 |
| 4,873,978 | 10/1989 | Ginsburg | 606/200 |
| 5,011,488 | 4/1991 | Ginsburg | 606/159 |
| 5,160,342 | 11/1992 | Reger et al. | 606/159 |
| 5,368,597 | 11/1994 | Pagedas | 606/127 |
| 5,423,830 | 6/1995 | Schneebaum et al. | 606/127 |
| 5,720,754 | 2/1998 | Middleman et al. | 606/127 |

FOREIGN PATENT DOCUMENTS

| | | | |
|---|---|---|---|
| 0156202 | 10/1985 | European Pat. Off. | 606/159 |
| 1049059 | 10/1983 | U.S.S.R. | 606/127 |

*Primary Examiner*—Michael H. Thaler
*Attorney, Agent, or Firm*—Hodgson, Russ, Andrews, Woods & Goodyear LLP

[57] ABSTRACT

The present invention relates to an apparatus for removal of a clot from a blood vessel comprising, an embolectomy catheter, one or more sheath introducers disposed within the embolectomy catheter, two removal devices moveably engaged within the sheath introducers, and a balloon catheter with an inflatable/deflatable balloon. Each removal device has a flexible rod and a racquet shaped head integral therewith. Each head has an attached basket for retaining the clot. Each head also has a wire extending from its distal end to the proximal end of the flexible rod for manipulation of the head during capture of the clot.

The invention also relates to a method for removing a clot from a blood vessel comprising the steps of: pre-loading two removal devices; one into each of two sheath introducers; pre-loading the two sheath introducers into an embolectomy catheter; making an incision for insertion of a guide wire into the right jugular vein; inserting the guide wire into the right jugular vein under an image amplifier; passing the guide wire into the pulmonary artery; inserting the preloaded embolectomy catheter into the jugular vein and passing the catheter over the guide wire to a point within the pulmonary artery proximate the clot; pushing the removal devices through a distal opening of the two sheath introducers and further through a distal opening of the embolectomy catheter; moving the removal devices toward the clot; capturing the clot between the removal devices; withdrawing the removal devices and the clot into the embolectomy catheter; and removing the embolectomy catheter from the vessel.

12 Claims, 9 Drawing Sheets

APPARATUS FOR REMOVING A BLOOD CLOT FROM A VESSEL

BACKGROUND OF THE INVENTION

A. Field of the Invention

The present invention relates to a method and apparatus for removing a blood clot from a vessel.

B. Description of the Prior Art

Venous thrombosis is the term used to describe a blood clot (thrombus) in a vein of the body. Most commonly these thrombi are found in the veins of the lower extremities; the thighs and calves. Thrombi found in veins deep in thighs or calves give rise to a condition called "deep vein thrombosis" (DVT). Venous thrombosis can occur in healthy as well as sick individuals.

A complication most commonly associated with venous thrombosis is the condition known as "pulmonary embolism." A pulmonary embolus is actually a clot that has broken free from a vein wall and has traveled to the pulmonary artery, then, if not removed, to a lung, causing blockage in an artery of that lung. When an embolus blocks a blood vessel in the lung, breathing is compromised and death may ensue.

It is estimated that in the United States each year, there are approximately 50,000 deaths resulting from pulmonary embolism. For this reason, pulmonary emboli must be removed from the pulmonary artery.

Many catheter systems are designed for percutaneous fragmentation of large pulmonary emboli. The devices generally consist of an impeller rotating at high speed at the end of the catheter for fragmentation of the clot While the developers of these apparatus often boast of quick and thorough fragmentation, particles in the effluent larger than 10 microns account for about 9% of the treated embolus weight. Such particles, once dislodged, may move into the lung and cause serious problems. Moreover, these catheter systems carry natural risks of damage to a vessel wall by the rotating impeller.

An apparatus and method are therefore needed to remove clots from blood vessels without rotating blades or fragmentation.

SUMMARY OF THE INVENTION

The present invention relates to an apparatus for removal of a clot from a vessel comprising, an embolectomy catheter, one or more sheath introducers disposed within the embolectomy catheter, two removal devices moveably engaged within the sheath introducers, and a balloon catheter with an inflatable/deflatable balloon. Each removal device has a flexible rod and a racquet shaped head integral therewith. The head has an attached basket for retaining the clot. The head also has a wire extending from its distal end to the proximal end of the flexible rod for manipulation of the head during capture of the clot.

The invention also relates to a method for removing a clot from a vessel comprising the steps of: pre-loading two removal devices, one into each of two sheath introducers; pre-loading the two sheath introducers into an embolectomy catheter; making an incision for insertion of a guide wire into the right jugular vein; inserting the guide wire into the right jugular vein under an image amplifier; passing the guide wire into the pulmonary artery; inserting the pre-loaded embolectomy catheter into the jugular vein and passing the catheter over the guide wire to a point within the pulmonary artery proximate the clot; pushing the removal devices through a distal opening of the two sheath introducers and further through a distal opening of the embolectomy catheter; moving the removal devices toward the clot; capturing the clot between the removal devices; withdrawing the removal devices and the clot into the embolectomy catheter; and removing the embolectomy catheter from the vessel.

It is a primary object of the present invention to provide an apparatus and method for removing thrombus from a vessel without fragmentation thereof.

It is a further object of the present invention to provide a removal apparatus which does not contain rotating impeller blades.

These and other objects will become apparent from the foregoing and ongoing written specification, the drawings, and the appended claims.

BRIEF DESCRIPTION OF THE DRAWINGS

The nature and mode of operation of the present invention will now be more fully described in the following detailed description taken with the accompanying drawings wherein.

DETAILED DESCRIPTION OF THE INVENTION

At the outset it should be clearly understood that like reference numerals are intended to identify the same structural elements, portions, or surfaces, consistently throughout the several drawing figures, as such elements, portions, or surfaces may be further described or explained by the entire written specification of which this detailed description is an integral part. Unless otherwise indicated, the drawings are intended to be read (e.g., arrangement of parts, mounting, etc.) together with the specification, and are to be considered a portion of the entire written description of this invention.

As used in the following description, the terms "horizontal," "vertical," "left," "right," "up," and "down," as well as adjectival and adverbial derivatives thereof (e.g., "horizontally," "rightwardly," "upwardly," etc.) simply refer to the orientation of the illustrated structure as the particular drawing figure faces the reader. The terms "proximate" and "proximal" refer to the end of the subject apparatus or part thereof, or position within a blood vessel closer to the incision and point of entry of the apparatus into the blood vessel, relative to the object or position compared with. The term "distal" refers to the end of the subject apparatus or part thereof, or position with a blood vessel farthest from the incision and point of entry of the apparatus into the blood vessel, relative to the object or position compared with.

Figure 1:
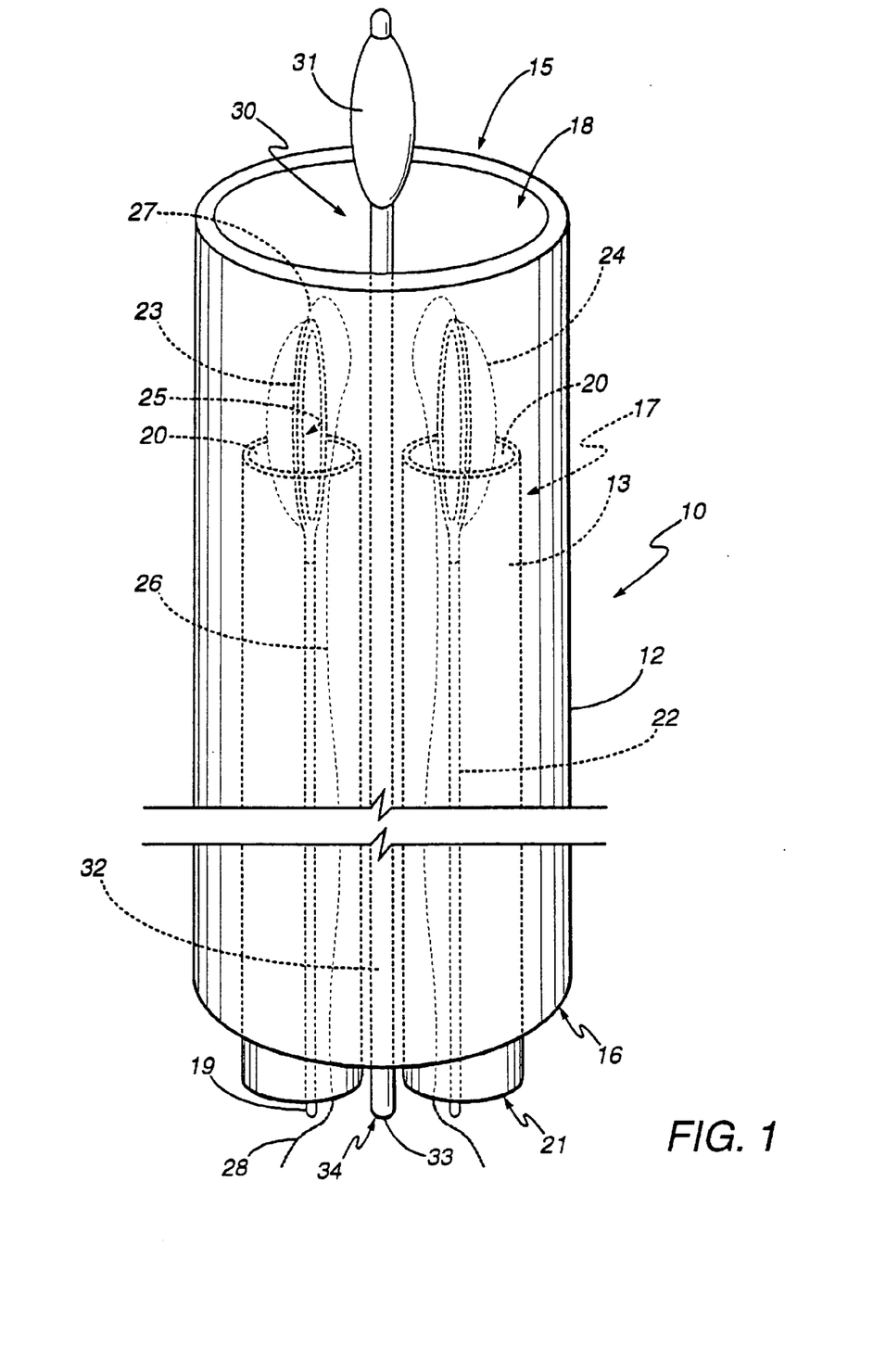
FIG. 1 is a perspective view of the present invention.
Figure 1A:
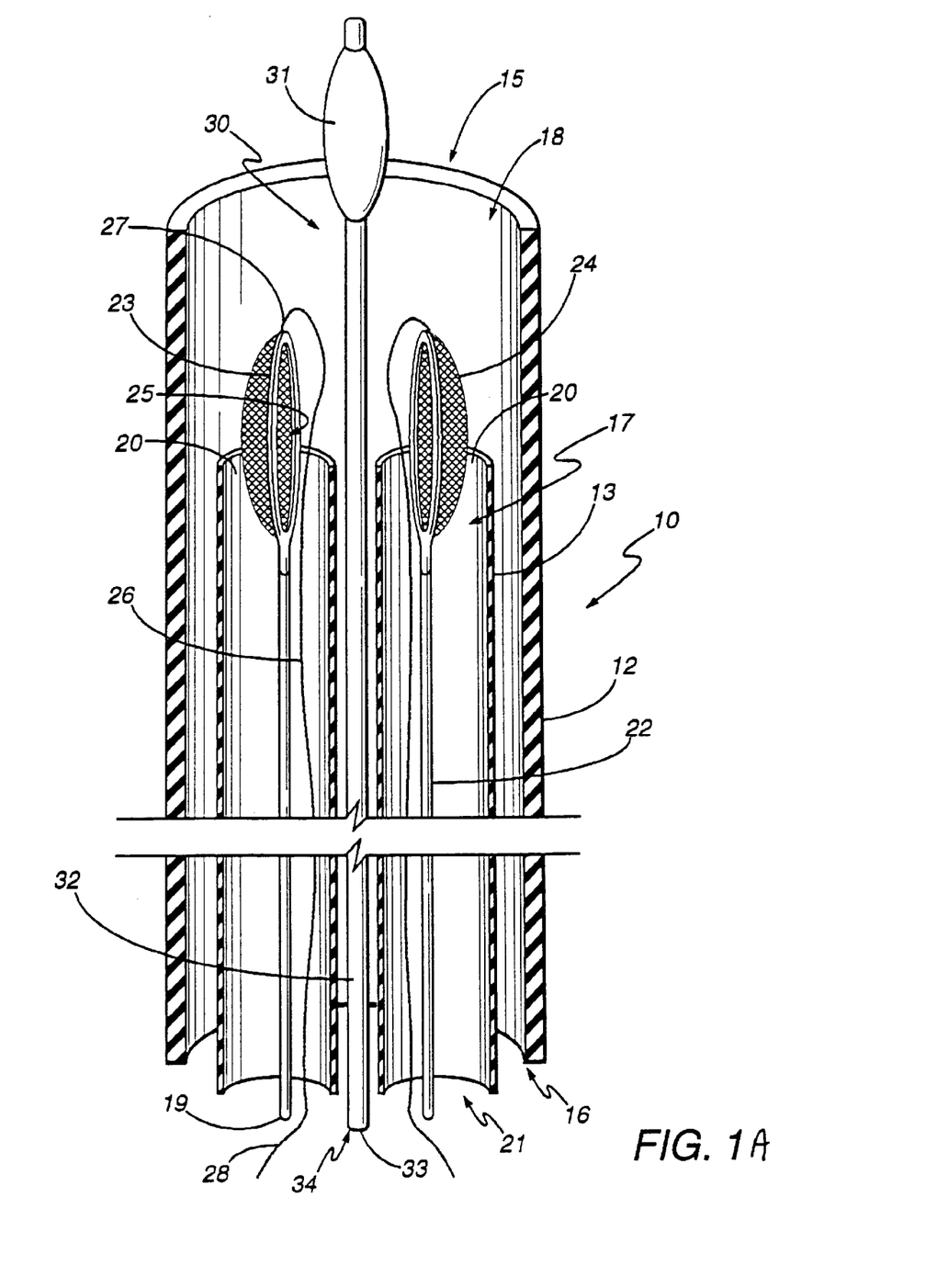
FIG. 1a is a cross sectional, perspective view of the present invention.

Referring to FIGS. 1 and 1a, apparatus 10, which may be used for removal of a clot from a blood vessel 11, is particularly useful for removing pulmonary emboli. Apparatus 10 is comprised of an embolectomy catheter 12 and one or more sheath introducers 13 disposed therewithin.

Embolectomy catheter 12 is preferably a flexible teflon or polyurethane material of sufficient length to pass from a point of entry through vessel 11 to a point proximate the clot 14 (shown in FIGS. 3–7). Furthermore, embolectomy catheter 12 contains a central lumen 18 having a distal opening 15 and a proximal opening 16.

As stated, and shown further in FIGS. 1 and 1a, preferably two sheath introducers 13 are disposed within central lumen 18 of embolectomy catheter 12. Sheath introducers 13, are used to carry removal devices 17 within central lumen 18 of embolectomy catheter 12 through vessel 11 for capture of clot 14. Since in its most preferred embodiment, two removal devices 17 are used with apparatus 10 for clot removal, it is preferred that embolectomy catheter 12 contain a separate sheath introducer 13 for each removal device 17. Another contemplated embodiment (not shown), however, uses one sheath introducer 13 sized to moveably house two removal devices 17.

Yet a third embodiment contemplated (not shown) is effectively a merger of sheath introducers 13 with embolectomy catheter 12 wherein sheath introducers 13 are fixedly engaged within lumen 18 of embolectomy catheter 13; much as a first and second separate lumen of embolectomy catheter 12.

Sheath introducers 13 are made up of a flexible material, preferably polyurethane or Teflon, and comprised of a distal opening 20 and a proximal opening 21.

Figure 2A:
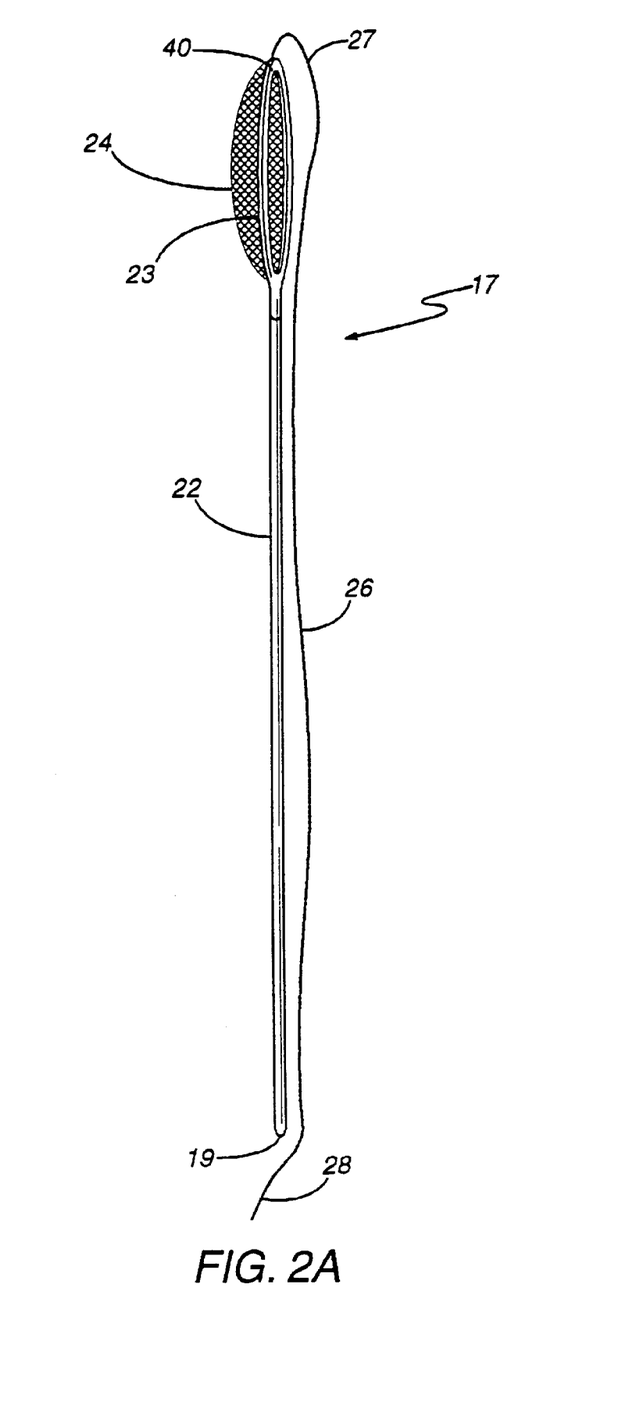
FIG. 2a is a perspective view of the present invention.
Figure 2B:
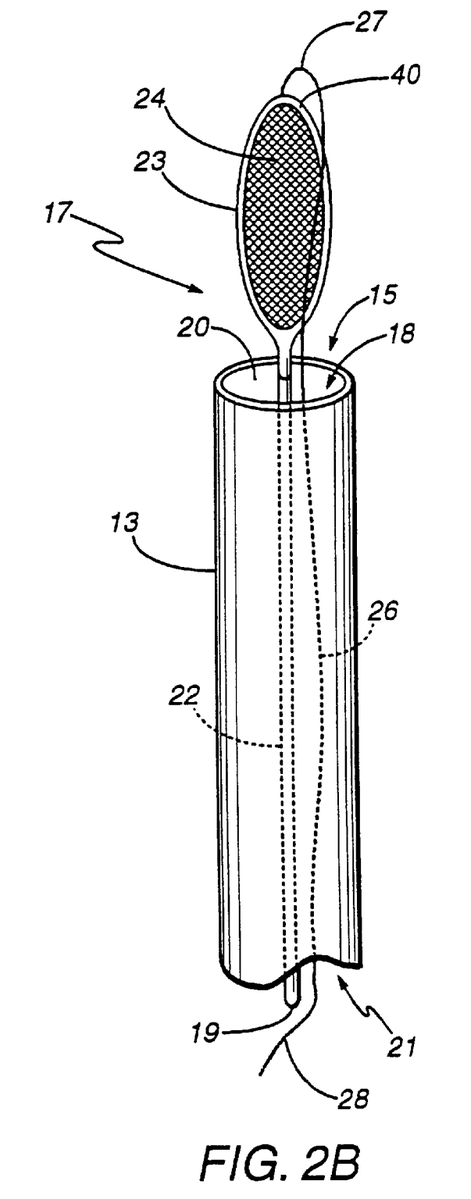
FIG. 2b is a perspective view of the present invention.
Figure 2C:
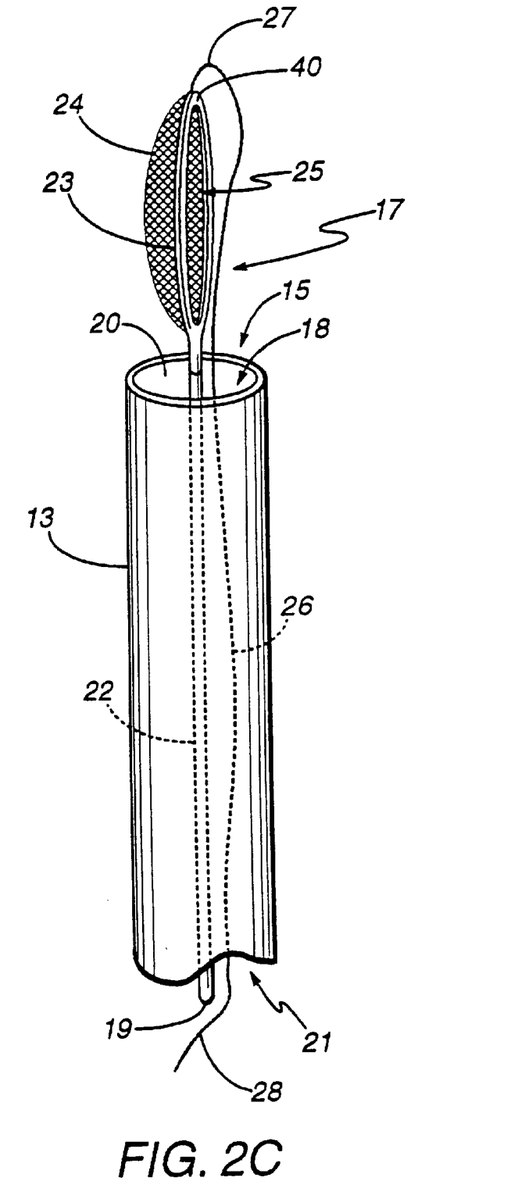
FIG. 2c is a perspective view of the present invention.

As indicated, apparatus 10 is further comprised of removal devices 17. These are pre-loaded within sheath introducer 13 for transport through vessel 11. Removal devices 17 may be comprised of plastic or stainless steel, or preferably Nitinol or other shape memory metal, and are compressible for pre-loading within sheath introducer 13. As depicted in FIGS. 2a 2b, and 2c, removal devices 17 are each further comprised of an elongated flexible rod 22, a racquet shaped head 23, and a non-crimped thin walled dacron or polyurethane basket 24 attached to head 23 in a manner to retain clot 14 between removal devices 17 after capture thereof.

In particular, basket 24 is preferably attached to the entire circumference of head 23 so as to eliminate any holes or gaps therebetween and cover the entire middle area 25 of head 23. Too, basket 24 is humped much like the bottom portion of a bowl for more secure retention of clot 14.

Removal device 17 further comprises a wire 26 extending from a distal end 40 of head 23 to a proximal end 19 of flexible rod 22 for manipulation of head 23 during the process of capturing clot 14 and retaining clot 14 within baskets 24. Specifically, wire 26 has a distal end 27 and a proximal end 28 and is of sufficient length to extend fully along flexible rod 22 and out of the vessel 11 at initial point of entry 9. Proximal end 28 of wire 26 may be pulled in appropriate directions to manipulate head 23. In this way, the two heads 23 may be maneuvered to grasp or capture clot 14, retain clot 14 within baskets 24, and pull clot 14 into embolectomy catheter 12 for removal from vessel 11. (see also FIGS. 6 and 7).

Referring again to FIGS. 1 and 1a, apparatus 10 may additionally comprise a balloon catheter 30 having an inflatable/deflatable balloon 31, preferably polyurethane, integral with its distal end, and a central lumen 32 in fluid communication therewith. Balloon catheter 30 is preferably a flexible material such as Teflon or polyurethane and further comprises an opening 33 at its proximal end 34 for injecting fluid into balloon 31 and for removing fluid therefrom; preferably with a syringe.

Figure 3:
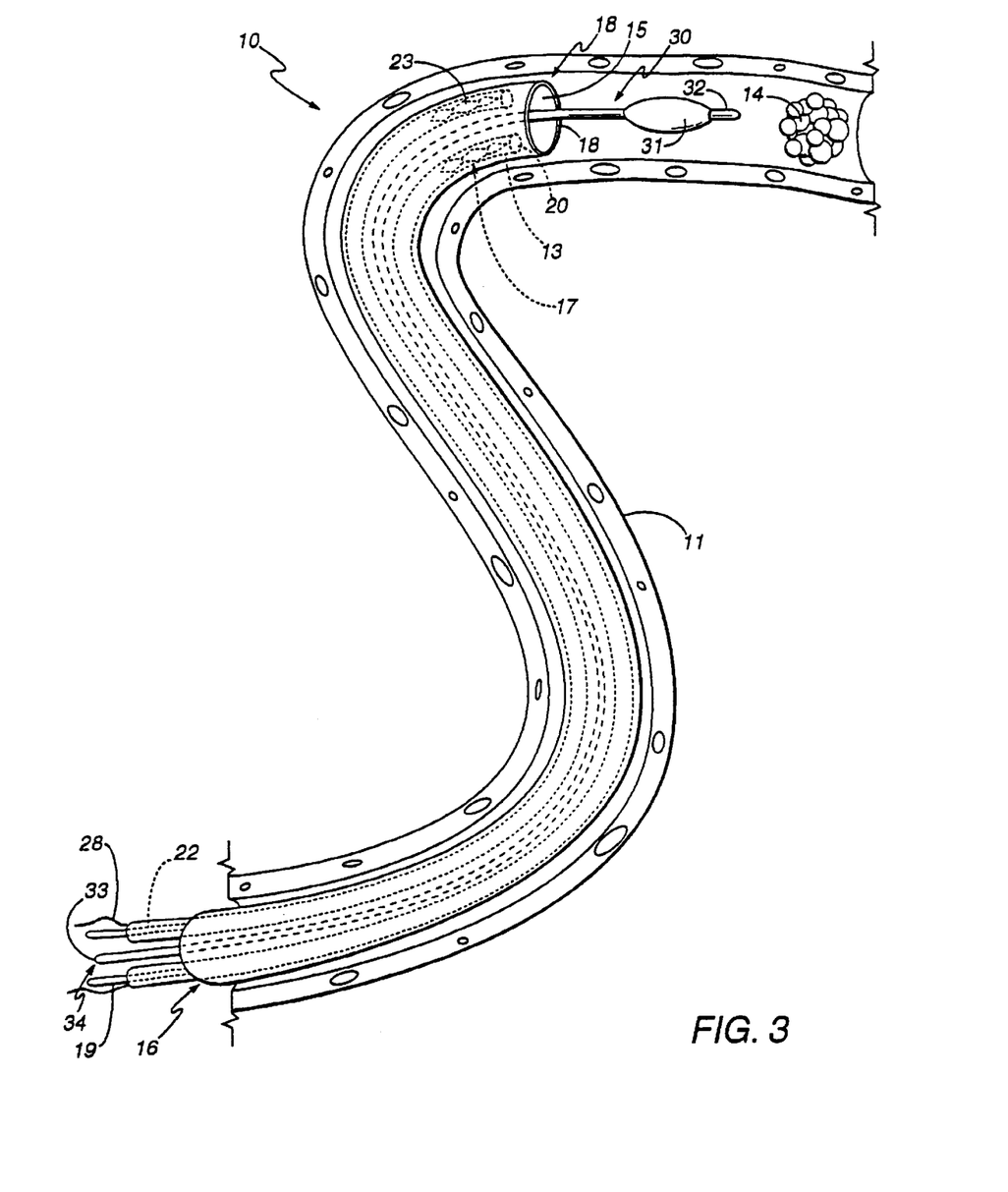
FIG. 3 is a perspective view of the present invention.
Figure 4:
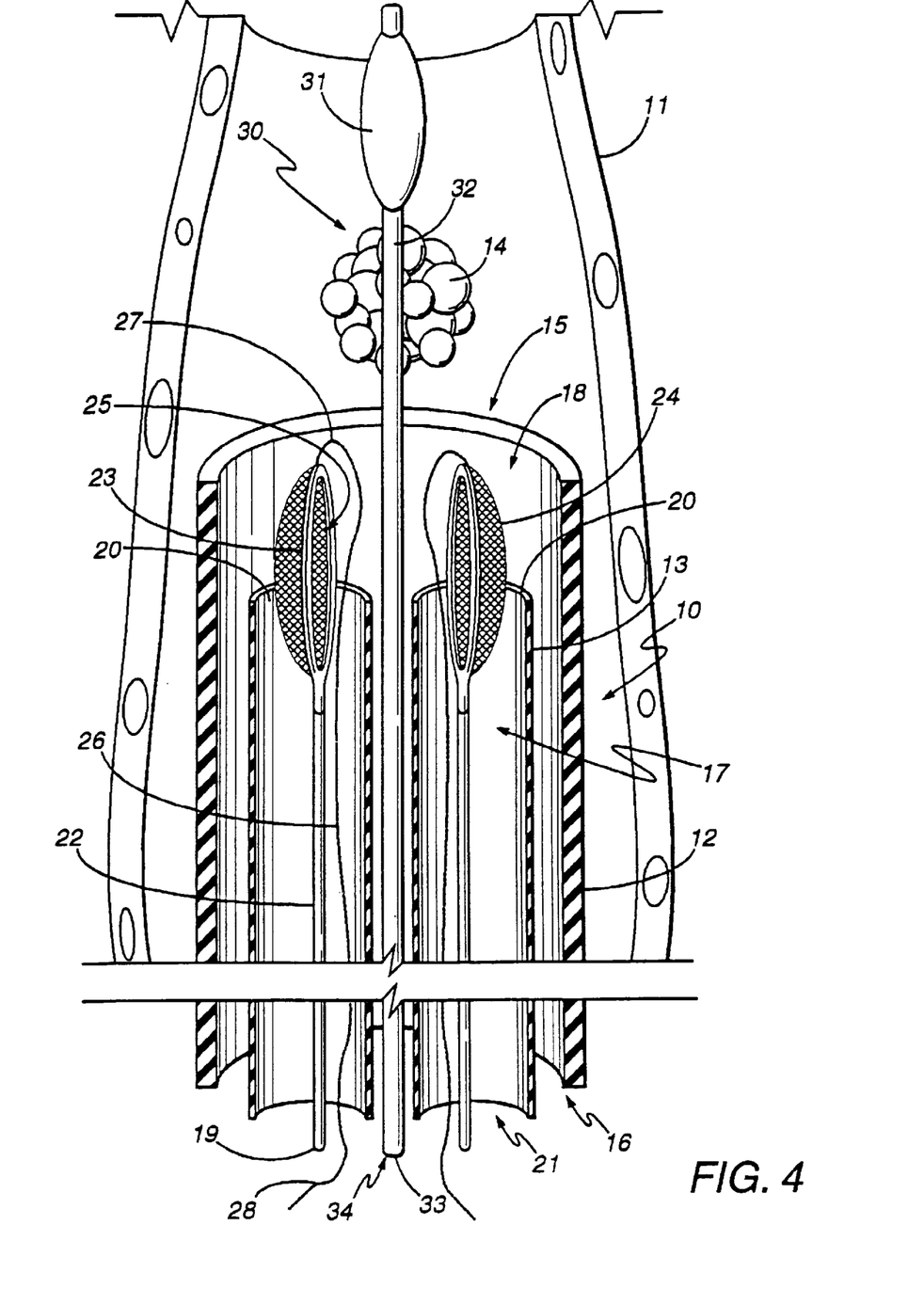
FIG. 4 is a cross sectional, perspective view of the present invention.
Figure 5:
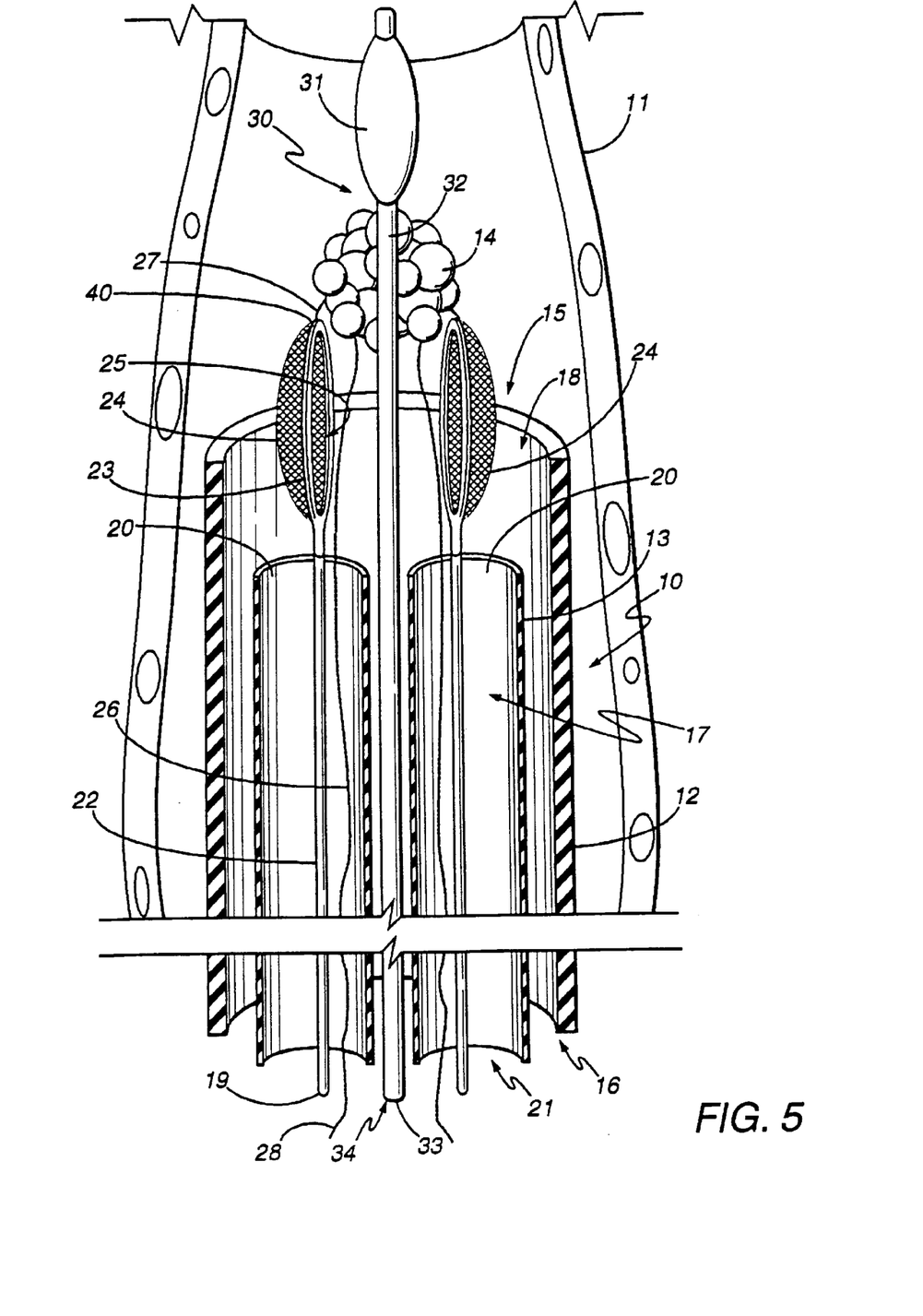
FIG. 5 is a cross sectional, perspective view of the present invention.

As shown in FIG. 3, in operation, one removal device 17 is pre-loaded into each of the two sheath introducers 13. The two sheath introducers 13 are then pre-loaded into an embolectomy catheter 12; that is, of course, unless introducers 13 are already fixed in the lumen of embolectomy catheter 12. A standard guide wire must be inserted into a vessel such as the right jugular vein then moved through the right jugular vein under an image amplifier. The guide wire is passed into the pulmonary artery to the area of clot 14.

As shown further in FIG. 3 and in FIGS. 4–7, the pre-loaded embolectomy catheter is then inserted into the jugular vein and passed over the guide wire to a point within pulmonary artery proximate clot 14. Balloon catheter 30 is then moved forward so that balloon 31 extends beyond clot 14 in the pulmonary artery. Removal devices 17 are then pushed through distal opening 20 of two sheath introducers 13 and further through distal opening 15 of embolectomy catheter 12, and into vessel 11. Removal devices 17 are then moved toward clot 14. Standard imaging is used to verify the location of removal devices 17 in relation to clot 14.

Figure 6:
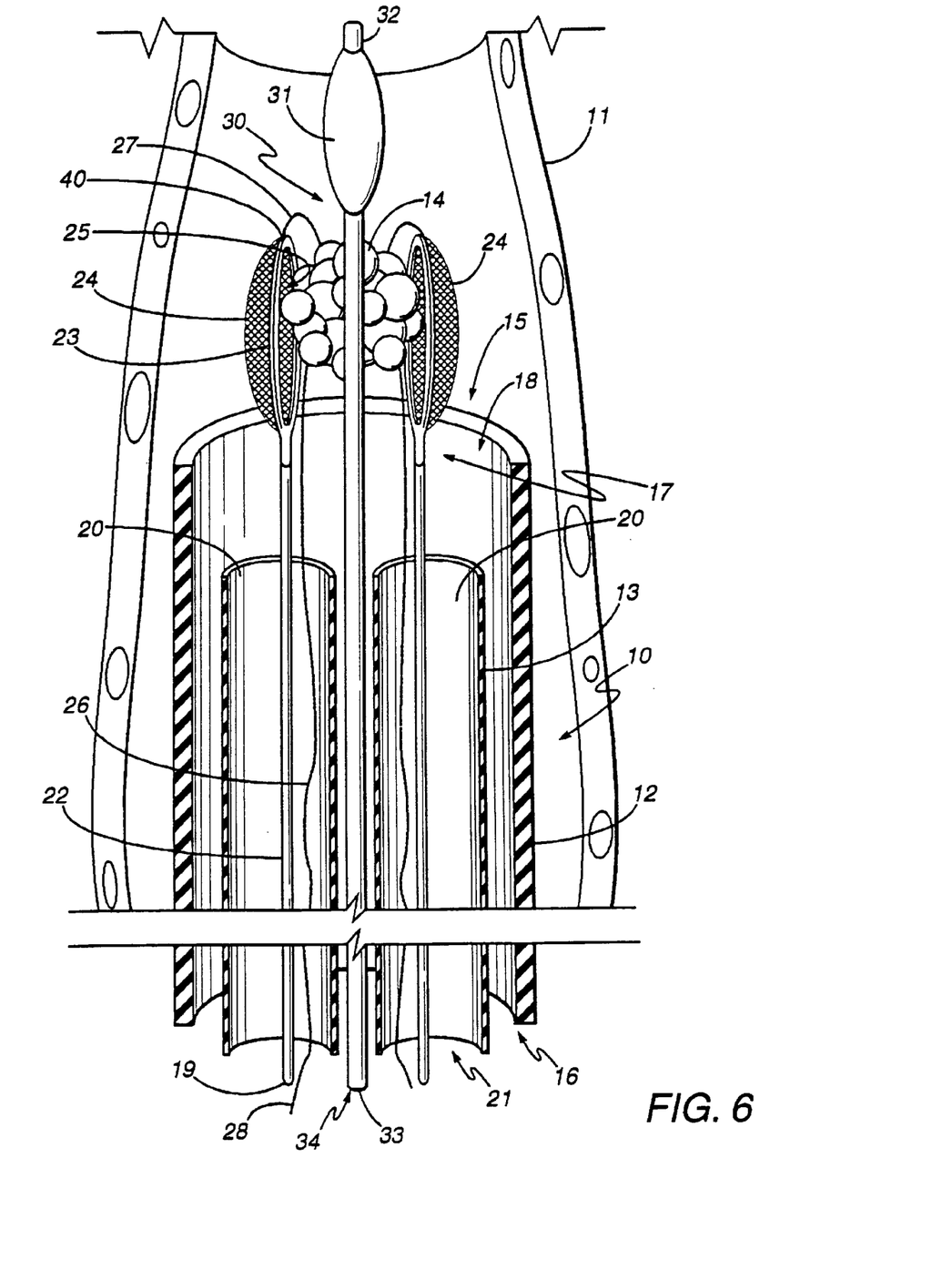
FIG. 6 is a cross sectional, perspective view of the present invention.
Figure 7:
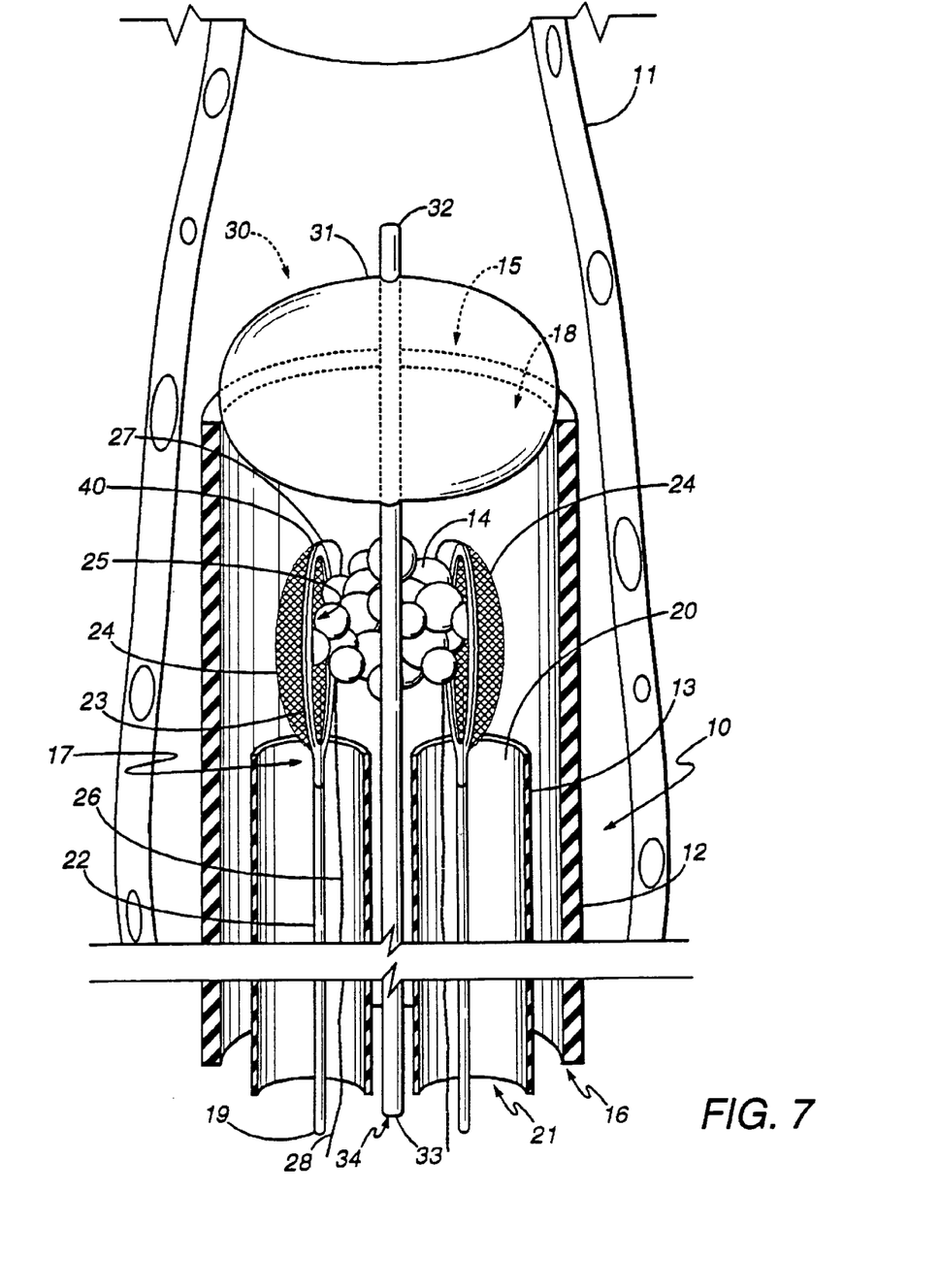
FIG. 7 is a cross sectional, perspective view of the present invention.

When removal devices 17 are appropriately positioned, heads 23 are manipulated by pulling proximal end 28 of wire 26 to capture and retain clot 14 between baskets 24 of heads 23. After clot 14 is secured between heads 23, proximal end 19 of flexible rod 22 is withdrawn and heads 23 with clot 14 are pulled into embolectomy catheter 12. Balloon catheter 30 may then be withdrawn a sufficient distance to place balloon 31 at opening 15 of embolectomy catheter 12 for inflation of balloon 31. Such inflation of balloon 31 will function to fully block opening 15 so that no part of clot 14 may escape. Apparatus 10 may then be fully removed from vessel 11 and incisions closed.

Therefore, while preferred forms of the method and apparatus have been shown and described, persons skilled in the art will readily appreciate that various additional changes and modifications may be made without departing from the spirit of the invention, as defined and differentiated by the following claims.

What is claimed is:

1. An apparatus for removal of a clot from a blood vessel, which comprises:

a) a first removal device comprising a first rod supporting a first container having a closed surrounding side wall extending to an open end of the first container at a distal end of the first rod;

b) a second removal device comprising a second rod supporting a second container having a closed surrounding side wall extending to an open end of the second container at a distal end of the second rod, wherein the first container faces the second container, and wherein the first and second removal devices are disposed inside a first catheter having a lumen extending to a distal open end, and wherein the first and second removal devices are movable along the lumen of the first catheter to extend out the distal open end thereof;

c) a wire extending from at least one of the first and second removal devices, wherein the wire is capable of being manipulated to cause the container of at least one of the removal devices to move toward the container of the other removal device to thereby contain the clot in the containers of the first and second removal devices; and d) a balloon catheter moveably disposed within the first catheter wherein the balloon catheter has an inflatable/deflatable balloon integral with a distal end of the balloon catheter having at least one lumen in fluid communication with the inflatable/deflatable balloon.

2. The apparatus of claim 1 wherein the first and second containers of the first and second removal devices each comprise a basket secured to an enclosing structure about an entire perimeter of the basket.

3. The apparatus of claim 2 wherein each of the enclosing structures of the first and second removal devices is substantially circular in shape.

4. The apparatus of claim 2 wherein the basket is of a screen material.

5. The apparatus of claim 2 wherein the first and second baskets are each dome-shaped members secured to an enclosing structure about an entire perimeter of the dome-shaped member to provide the first and second containers.

6. The apparatus of claim 5 wherein the dome-shaped member is of Dacron or polyurethane.

7. The apparatus of claim 1 wherein the wire is connected to a distal portion of the at least one of the first and second containers.

8. The apparatus of claim 1 wherein there is a wire connected to a distal portion of both the first and second containers.

9. The apparatus of claim 1 wherein the first rod and the second rod of the first and second removal devices are flexible.

10. The apparatus of claim 9 wherein the first and second removal devices are disposed inside respective first and second sheaths positioned inside the lumen of the first catheter.

11. The apparatus of claim 9 wherein the first catheter is flexible.

12. An apparatus for removal of a clot from a blood vessel, which comprises:

a) a first catheter having a central lumen extending to a distal open end thereof;

b) a first sheath disposed inside the first catheter, wherein the first sheath houses a first removal device movably disposed within a lumen of the first sheath and comprising a first rod supporting a first container having a closed surrounding side wall extending to an open end of the first container at a distal end of the first rod;

c) a second sheath disposed inside the first catheter, wherein the second sheath houses a second removal device movably disposed within a lumen of the second sheath and comprising a second rod supporting a second container having a closed surrounding side wall extending to an open end of the second container at a distal end of the second rod;

d) a wire extending from at least one of the first and second removal devices, wherein the wire is capable of being manipulated to cause the container of at least one of the removal devices to move toward the container of the other removal device to thereby contain the clot in the containers of the first and second removal devices; and e) a balloon catheter movably disposed within the first catheter and supporting a balloon at a distal end thereof, wherein the balloon catheter is extendable out the distal open end of the first catheter and beyond the location of a clot to inflate the balloon and block the blood vessel and wherein the first and second removal devices are movable out of their respective sheaths to a position disposed on either side of the clot and wherein the wire is capable of being manipulated to cause the container of at least one of the removal devices to move toward the container of the other removal device to thereby contain the clot in the containers of the first and second removal devices.

* * * * *